(12) United States Patent
Zuo et al.

(10) Patent No.: US 7,996,154 B2
(45) Date of Patent: *Aug. 9, 2011

(54) METHODS AND APPARATUS FOR ANALYSIS OF DOWNHOLE ASPHALTENE GRADIENTS AND APPLICATIONS THEREOF

(75) Inventors: Youxiang (Julian) Zuo, Edmonton (CA); Oliver C. Mullins, Ridgefield, CT (US); Jinglin Gao, Edmonton (CA); Abdel M. Kharrat, Edmonton (CA); Kentaro Indo, Edmonton (CA); Michael O'Keefe, Blackmans Bay (AU); Soraya S. Betancourt, Cambridge, MA (US); Chengli Dong, Sugar Land, TX (US); Francois Dubost, Idron (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 431 days.

This patent is subject to a terminal disclaimer.

(21) Appl. No.: 12/352,369

(22) Filed: Jan. 12, 2009

(65) Prior Publication Data

US 2009/0248310 A1    Oct. 1, 2009

Related U.S. Application Data

(60) Provisional application No. 61/040,042, filed on Mar. 27, 2008.

(51) Int. Cl.
*G01V 1/40* (2006.01)
*G01V 1/00* (2006.01)

(52) U.S. Cl. .......... 702/11; 702/6; 706/14; 706/21; 175/40; 175/58

(58) Field of Classification Search .......... 702/11, 702/6; 706/14, 21; 175/40, 58
See application file for complete search history.

(56) References Cited

U.S. PATENT DOCUMENTS

| | | | |
|---|---|---|---|
| 3,859,851 A | 1/1975 | Urbanosky | |
| 4,994,671 A | 2/1991 | Safinya et al. | |
| 5,167,149 A | 12/1992 | Mullins et al. | |
| 5,201,220 A | 4/1993 | Mullins et al. | |
| 5,266,800 A | 11/1993 | Mullins | |
| 5,331,156 A | 7/1994 | Mullins | |
| 6,467,340 B1 | 10/2002 | Gallagher et al. | |
| 7,461,547 B2 | 12/2008 | Mullins | |
| 7,822,554 B2 * | 10/2010 | Zuo et al. | 702/6 |

FOREIGN PATENT DOCUMENTS

| | | |
|---|---|---|
| SU | 1260904 | 9/1986 |
| SU | 1702795 | 5/1995 |

OTHER PUBLICATIONS

Hirschberg, Avraham: "Role of Asphaltenes in Compositional Grading of a Reservoir's Fluid Column", Journal of Petroleum Technology, Jan. 1988, pp. 89-94.

(Continued)

*Primary Examiner* — Bryan Bui
(74) *Attorney, Agent, or Firm* — Jay P. Sbrollini; Wayne I. Kanak (57) ABSTRACT

A method and system for characterizing asphaltene gradients of a reservoir of interest and analyzing properties of the reservoir of interest based upon such asphaltene gradients. The analysis employs a correlation that relates insoluble asphaltene concentration to spectrophotometry measurement data measured at depth.

20 Claims, 4 Drawing Sheets

OTHER PUBLICATIONS

Hoier, Lars et al: "Compositional Grading—Theory and Practice", Society of Petroleum Engineers, Oct. 2000, pp. 1-16, SPE 63085.

Li, Yinghui and Johns, Russell T: "Rapid Flash Calculations for Compositional Simulation", Society of Petroleum Engineers, Oct. 2006, SPE 95732.

Montel, Francois et al : "Initial state of petroleum reservoirs: A comprehensive approach", Journal of Petroleum Science & Engineering, Mar. 12, 2006, pp. 391-402.

Montel, Francois et al: "Modeling the Effect of External Gas Flux on Reservoir Fluid Distribution", Society of Petroleum Engineers, Sep.-Oct. 2002, pp. 1-6, SPE 77383.

Montel, Francois et al: "Prediction of Compositional Grading in a Reservoir Fluid Column", Society of Petroleum Engineers, Sep. 1985, pp. 1-12, SPE 14410.

Montel, Francois et al: "Pressure and Compositional Gradients in Reservoirs", Society of Petroleum Engineers, Aug. 2003, pp. 1-8, SPE 85668.

Pedersen, K.S. et al: "Modeling of Large Hydrocarbon Compositional Gradient", Society of Petroleum Engineers, Nov. 2006, pp. 1-7, SPE 101275.

Pedersen, K.S. et al: "Simulations of Compositional Gradients in Hydrocarbon Reservoirs Under the Influence of a Temperature Gradient", Society of Petroleum Engineers, Oct. 2003, pp. 1-10, SPE 84364.

Ratulowski, J. et al: "Theoretical and Experimental Investigation of Isothermal Compositional Grading", SPE Reservoir Evaluation & Engineering, Jun. 2003, pp. 168-175.

Schulte, A.M.: "Compositional Variations Within a Hydrocarbon Column due to Gravity", Society of Petroleum Engineers of AIME, Sep. 1980, pp. 1-10, 9235.

Smith, Richard W. et al: "Equation of State of a Complex Fluid Column and Prediction of Contacts in Orocual Field, Venezuela", Society of Petroleum Engineers, Oct. 2000, SPE 63088.

Wang, P. et al: "A New Generation EOS Compositional Reservoir Simulator: Part I—Formulation and Discretization", Society of Petroleum Engineers, 1997, SPE 37979.

Almehaideb, Reyadh A. et al: "EOS tuning to model full field crude oil properties using multiple well fluid PVT analysis", Journal of Petroleum Science and Engineering, 2000, vol. 26, Issues 1-4, pp. 291-300.

* cited by examiner

METHODS AND APPARATUS FOR ANALYSIS OF DOWNHOLE ASPHALTENE GRADIENTS AND APPLICATIONS THEREOF

CROSS-REFERENCE TO RELATED APPLICATIONS

This application claims priority from U.S. Provisional Application 61/040,042, filed Mar. 27, 2008, which is incorporated herein by reference.

BACKGROUND OF THE INVENTION

1. Field of the Invention

The present invention relates to methods and apparatus for characterizing petroleum fluid extracted from a hydrocarbon-bearing geological formation. The invention has application to reservoir simulation applications, although it is not limited thereto.

2. Description of Related Art

Petroleum consists of a complex mixture of hydrocarbons of various molecular weights, plus other organic compounds. The exact molecular composition of petroleum varies widely from formation to formation. The proportion of hydrocarbons in the mixture is highly variable and ranges from as much as 97 percent by weight in the lighter oils to as little as 50 percent in the heavier oils and bitumens. The hydrocarbons in petroleum are mostly alkanes (linear or branched), cycloalkanes, aromatic hydrocarbons, or more complicated chemicals like asphaltene. The other organic compounds in petroleum typically contain carbon dioxide ($CO_2$), nitrogen, oxygen, and sulfur, and trace amounts of metals such as iron, nickel, copper, and vanadium.

The alkanes, also known as paraffins, are saturated hydrocarbons with straight or branched chains which contain only carbon and hydrogen and have the general formula $C_nH_{2n+2}$. They generally have from 5 to 40 carbon atoms per molecule, although trace amounts of shorter or longer molecules may be present in the mixture. The alkanes include methane ($CH_4$), ethane ($C_2H_6$), propane ($C_3H_8$), i-butane ($iC_4H_{10}$), n-butane ($nC_4H_{10}$), i-pentane ($iC_5H_{12}$), n-pentane ($nC_5H_{12}$), hexane ($C_6H_{14}$), heptane ($C_7H_{16}$), octane ($C_8H_{18}$), nonane ($C_9H_{20}$), decane ($C_{10}H_{22}$), hendecane ($C_{11}H_{24}$)—also referred to as endecane or undecane, dodecane ($C_{12}H_{26}$), tridecane ($C_{13}H_{28}$), tetradecane ($C_{14}H_{30}$), pentadecane ($C_{15}H_{32}$), and hexadecane ($C_{16}H_{34}$).

The cycloalkanes, also known as napthenes, are saturated hydrocarbons which have one or more carbon rings to which hydrogen atoms are attached according to the formula $C_nH_{2n}$. Cycloalkanes have similar properties to alkanes but have higher boiling points. The cycloalkanes include cyclopropane ($C_3H_6$), cyclobutane ($C_4H_8$), cyclopentane ($C_5H_{10}$), cyclohexane ($C_6H_{12}$), cycloheptane ($C_7H_{14}$), etc.

The aromatic hydrocarbons are unsaturated hydrocarbons which have one or more planar six-carbon rings called benzene rings, to which hydrogen atoms are attached with the formula $C_nH_n$. They tend to burn with a sooty flame, and many have a sweet aroma. Some are carcinogenic. The aromatic hydrocarbons include benzene ($C_6H_6$) and derivatives of benzene, as well as polyaromatic hydrocarbons.

Asphaltenes consist primarily of carbon, hydrogen, nitrogen, oxygen, and sulfur, as well as trace amounts of vanadium and nickel. The C:H ratio is approximately 1:1.2, depending on the asphaltene source. Asphaltenes have been shown to have a distribution of molecular masses in the range of 400 to 1500 grams/mole with a maximum around 750 grams/mole. The chemical structure of asphaltene is difficult to ascertain due to its complex nature, but has been studied by existing techniques. It is undisputed that asphaltene is composed mainly of polyaromatic carbon, i.e. polycondensed aromatic benzene units with oxygen, nitrogen, and sulfur, combined with minor amounts of a series of heavy metals, particularly vanadium and nickel, which occur in porphyrin structures. Asphaltenes are today widely recognized as soluble, chemically-altered fragments of kerogen which migrated out of the source rock during oil catagenesis. Asphaltenes are dispersed in reservoir petroleum fluid as nanoaggregates. Heavy oils and tar sands contain much higher proportions of asphaltenes than do medium-API oils or tight oils. Condensates are virtually devoid of asphaltenes.

Computer-based modeling and simulation techniques have been developed for estimating the properties and/or behavior of petroleum fluid in a reservoir of interest. Typically, such techniques employ an equation of state (EOS) model that represents the phase behavior of the petroleum fluid in the reservoir. Once the EOS model is defined, it can be used to compute a wide array of properties of the petroleum fluid of the reservoir, such as gas-oil ratio (GOR) or condensate-gas ratio (CGR), density of each phase, volumetric factors and compressibility, heat capacity and saturation pressure (bubble or dew point). Thus, the EOS model can be solved to obtain saturation pressure at a given temperature. Moreover, GOR, CGR, phase densities, and volumetric factors are byproducts of the EOS model. Transport properties, such as heal capacity or viscosity, can be derived from properties obtained from the EOS model, such as fluid composition. Furthermore, the EOS model can be extended with other reservoir evaluation techniques for compositional simulation of flow and production behavior of the petroleum fluid of the reservoir, as is well known in the art. For example, compositional simulations can be helpful in studying (1) depletion of a volatile oil or gas condensate reservoir where phase compositions and properties vary significantly with pressure below bubble or dew point pressures, (2) injection of gas (dry or enriched) into a black oil reservoir to mobilize oil by vaporization into a more mobile gas phase or by condensation through an outright (single-contact) or dynamic (multiple-contact) miscibility, and (3) injection of $CO_2$ into an oil reservoir to mobilize oil by miscible displacement and by oil viscosity reduction and oil swelling.

In the past few decades, fluid homogeneity in a hydrocarbon reservoir has been assumed. However, there is now a growing awareness that fluids are often heterogeneous or compartmentalized in the reservoir. A compartmentalized reservoir consists of two or more compartments that may not be in hydraulic communication. Two types of reservoir compartmentalization have been identified, namely vertical and horizontal compartmentalization. Vertical compartmentalization usually occurs as a result of layering or stratigraphic changes in the reservoir, while horizontal compartmentalization results from faulting.

Molecular and thermal diffusion, natural convection, biodegradation, adsorption, and external fluxes can also lead to non-equilibrium hydrocarbon distribution in a reservoir.

Reservoir compartmentalization, as well as non-equilibrium hydrocarbon distribution, can significantly hinder production and can make the difference between an economically-viable field and an economically-nonviable field. Techniques to aid an operator to accurately describe reservoir compartments and their distribution as well as non-equilibrium hydrocarbon distribution can increase understanding of such reservoirs and ultimately raise production.

Downhole fluid analysis (DFA) measurements provide a useful tool to determine the compositional gradients at downhole conditions in real time. An example of a well logging tool suitable for capturing fluid samples for compositional data analysis is the Modular Formation Dynamics Tester (MDT) (available from Schlumberger Technology Corporation of Sugar Land, Tex. USA). The MDT tool provides a controlled channel of hydraulic communication between the reservoir fluid and the wellbore and allows withdrawal of small amounts of formation fluid through a probe that contacts the reservoir rock (formation). Such downhole fluid sampling is advantageous because the sampling is more accurate downhole. More specifically, in the event that the sampling pressure is above the saturation pressure, the fluid will be in a single phase, ensuring that the original composition is being analyzed. For pressures below the saturation pressure, a measurement of the properties of the liquid phase in the oil zone and the associated gas above it will yield a more accurate sampling than a sample recombined at surface. Indeed, it may be difficult to retain the sample in the state in which it existed downhole when it is retrieved to surface. Historically, fluid samples collected by well logging tools were brought to the surface for analysis in the laboratory. However, recent developments in the MDT tool have made possible the direct measurement of fluid properties downhole during the pumpout or sampling sequence, which is referred to herein as "downhole fluid analysis." Details of the MDT tool and its capabilities for downhole fluid analysis may be obtained with reference to U.S. Pat. Nos. 3,859,851; 4,994,671; 5,167,149; 5,201,220; 5,266,800; and 5,331,156, all of which are incorporated herein by reference.

Downhole fluid analysis is advantageous because information is provided in real time, in contrast to a laboratory analysis that may last for several days or surface wellsite analysis that may result in undesirable phase transitions as well as the loss of key constituents. However, the compositional and property gradients (e.g., the compositions of $CO_2$, $C_1$, $C_2$, $C_3$-$C_5$, and $C_{6+}$, and gas-oil ratio (GOR)) measured by such DFA tools may not provide information that can be used to accurately detect compartmentalization and/or non-equilibrium hydrocarbon distribution in the reservoir of interest.

BRIEF SUMMARY OF THE INVENTION

It is therefore an object of the invention to provide methods and apparatus for downhole fluid analysis that are able to accurately detect compartmentalization and/or non-equilibrium hydrocarbon distribution in the reservoir of interest.

It is yet another object of the invention to provide methods and apparatus for downhole fluid analysis that predict asphaltene content with depth and use such predictions to compare against downhole measurements associated therewith in order to accurately detect compartmentalization and/ or non-equilibrium hydrocarbon distribution in the reservoir of interest.

It is still another object of the present invention to provide methods and apparatus for interpreting downhole fluid analysis to estimate downhole asphaltene components over depth using an equation-of-state (EOS) approach, and for determining compartmentalization or non-equilibrium of the reservoir based on such estimates.

In accord with the objects of the invention, a downhole fluid analysis tool is employed to perform compositional measurements at one measurement station (reference point) and possibly other measurement stations within a wellbore traversing a reservoir of interest. Compositional and asphaltene gradients with depth can be predicted with equations of state (EOS) that take into account, for example, the impacts of gravitational forces, chemical forces, and thermal diffusion. The EOS can employ a well-known flash approach in order to predict asphaltene content of live oil at downhole conditions at depth. The predicted asphaltene content can then be associated with a prediction of spectrophotometry measurements performed by the DFA tool at the given depth by a correlation between such values. The predicted and actual spectrophotometry measurements at the given depth can then be compared to one another to determine reservoir properties (such as compartmentalization or non-equilibrium, and layer connectivity or equilibrium).

Additional objects and advantages of the invention will become apparent to those skilled in the art upon reference to the detailed description taken in conjunction with the provided figures.

DETAILED DESCRIPTION OF THE INVENTION

As used herein, the term "dead oil" refers to petroleum fluid at sufficiently low pressure that it contains no dissolved gas, or a relatively thick petroleum fluid or residue that has lost its volatile components.

As used herein, the term "live oil" refers to petroleum fluid containing dissolved gas in solution that may be released from solution at surface conditions.

Figure 1:
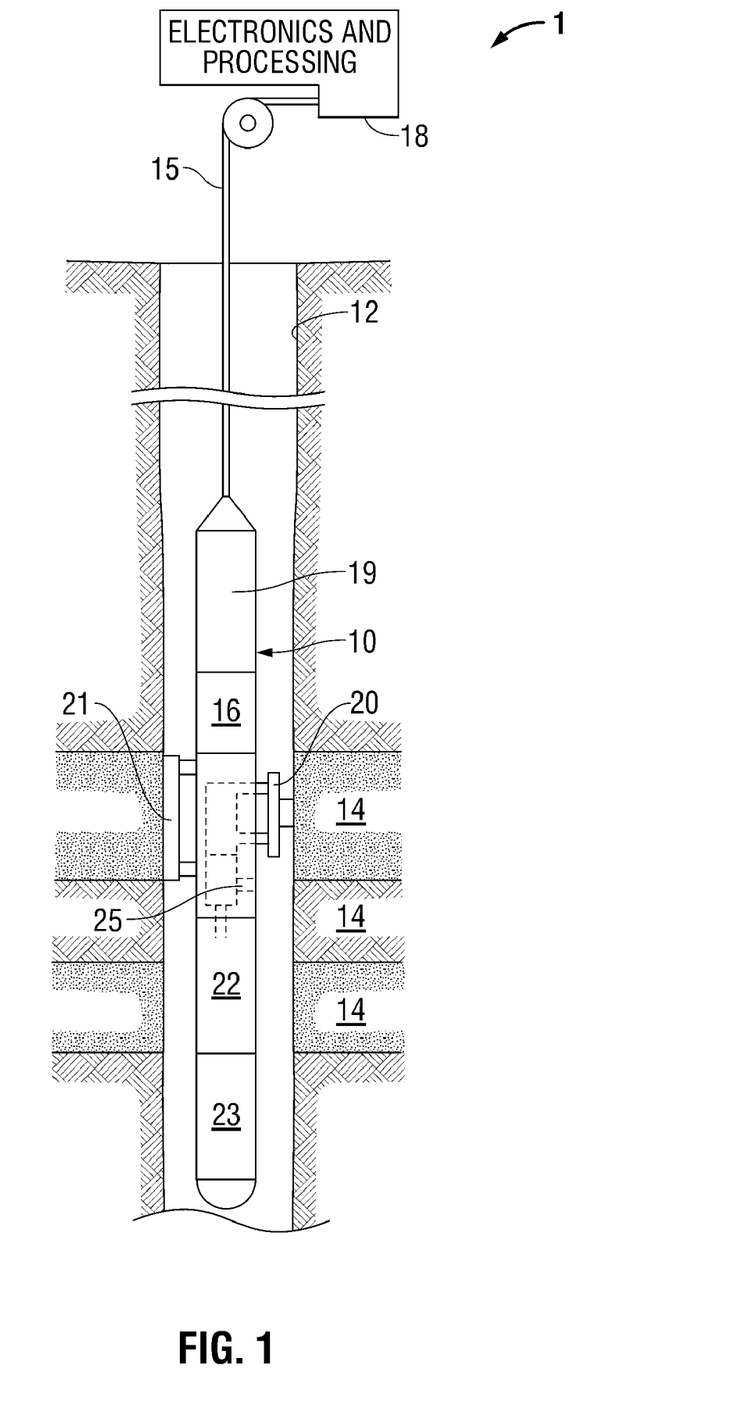
FIG. 1 is a schematic diagram of an exemplary petroleum reservoir analysis system in which the present invention is embodied.

FIG. 1 illustrates an exemplary petroleum reservoir analysis system 1 in which the present invention is embodied. The system 1 includes a borehole tool 10 suspended in the borehole 12 from the lower end of a typical multiconductor cable 15 that is spooled in a usual fashion on a suitable winch (not shown) on the formation surface. The cable 15 is electrically coupled to an electrical control system 18 on the formation surface. The tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the elongated body 19. The fluid admitting assembly 20 is equipped for selectively sealing off or isolating selected portions of the wall of the borehole 12 such that pressure or fluid communication with the adjacent earth formation 14 is established. Also included with tool 10 are means for determining the downhole pressure and temperature (not shown) and a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis module, and the flow path to the collecting chambers is maintained by the electrical control systems 16 and 18. As will be appreciated by those skilled in the art, the surface-located electrical control system 18 includes data processing functionality (e.g., one or more microprocessors, associated memory, and other hardware and/or software) to implement the invention as described herein. The electrical control system 18 can also be realized by a distributed data processing system wherein data measured by the tool 10 is communicated (preferably in real-time) over a communication link (typically a satellite link) to a remote location for data analysis as described herein. The data analysis can be carried out on a workstation or other suitable data processing system (such as a computer cluster or computing grid).

Detailed downhole and laboratory analyses of crude oils show apparent correspondence between asphaltene gradients with depth and compartmentalization and/or non-equilibrium hydrocarbon distribution in the reservoir. However, the DFA tool of FIG. 1 (as well as other current DFA tools) does not measure asphaltene content directly, but instead measures concentrations of light fractions (e.g., methane ($CH_4$) and ethane ($C_2H_6$)) as well the C3-C5 alkane group and the lump of hexane and heavier alkane components (C6+). Such measurements are based on spectrophotometry measurements (i.e., the absorption spectra of the downhole fluid sample).

In accordance with the present invention, the apparatus of FIG. 1 is employed to perform compositional measurements at one measurement station (reference point) and possibly other measurement stations within a wellbore traversing a reservoir of interest. Compositional and asphaltene gradients with depth can be predicted with equations of state (EOS) that take into account the impacts of, for example, gravitational forces, chemical forces, and thermal diffusion. The EOS can employ a well-known Hash approach in order to predict asphaltene content of live oil at downhole conditions at depth. The predicted asphaltene content can then be associated with a prediction of spectrophotometry measurements performed by the DFA tool of FIG. 1 at the given depth by a correlation between such values. The predicted and actual spectrophotometry measurements at the given depth can then be compared to one another to determine reservoir compartmentalization or non-equilibrium.

Figure 2:
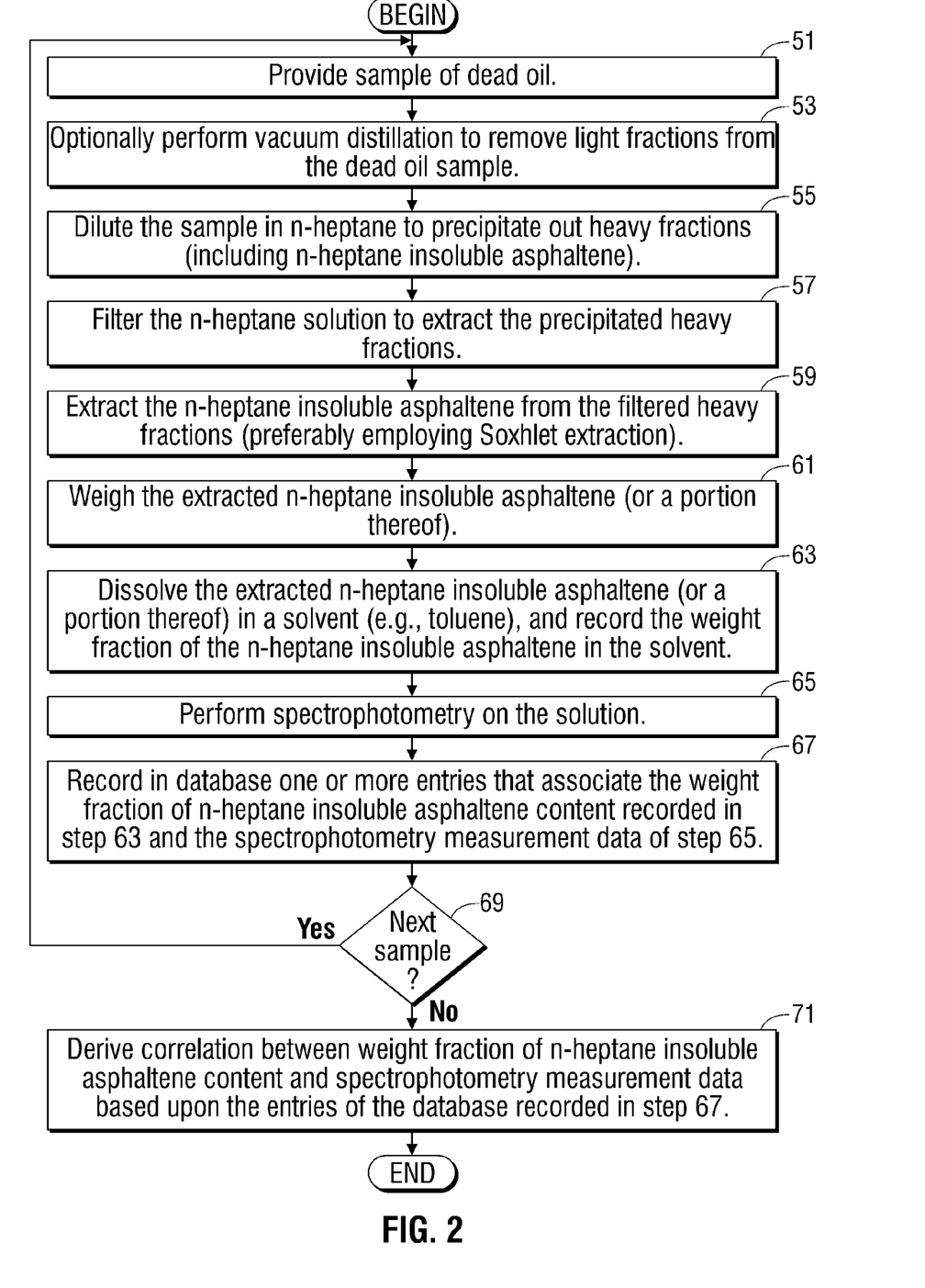
FIG. 2 is a flow chart of operations for deriving and storing correlations between weight fractions of asphaltene content and spectrophotometry measurement data.

The methodology summarized above requires a correlation mechanism that relates asphaltene content at downhole conditions to spectrophotometry measurement results associated therewith. FIG. 2 illustrates an exemplary methodology for deriving and storing such a correlation mechanism. The operations begin at step 51 by providing a sample of dead oil. At optional step 53, the sample can be subject to vacuum distillation (also referred to as "topping") to remove light fractions from the dead oil sample. In step 55, the sample is diluted in n-heptane to precipitate out heavy fractions (including n-heptane insoluble asphaltene). In step 57, the n-heptane solution is filtered with to extract the heavy fractions precipitated in step 55. In step 59, n-heptane insoluble asphaltene is extracted from the heavy fractions filtered in step 57, preferably by Soxhlet extraction. In step 61, the n-heptane insoluble asphaltene extracted in step 59 (or a portion thereof) is weighed. In step 63, the n-heptane insoluble asphaltene extracted in step 59 (or a portion thereof) is dissolved in a suitable solvent (preferably toluene) and the weight fraction of the n-heptane insoluble asphaltene in the solution is recorded. In step 65, the solution of step 63 is subject to spectrophotometry, which measures the absorption spectra of the solution. In step 67, the weight fraction of n-heptane insoluble asphaltene recorded in step 63 is associated with the spectrophotometry measurement results of 65 as part of one or more records in a database. In step 69, the operations determine if there are other samples to process. In the preferred embodiment, the process is carried out over a number of samples from different geographic areas of the world. If there are additional samples to process, the operation returns to step 51 to process the next sample. Otherwise, the operations continue to step 71 to derive a correlation between weight fraction of n-heptane insoluble asphaltene content and the spectrophotometry measurement data associated therewith as part of the database recorded in step 67. The correlation can be realized by a neural network trained by the weight fractions of n-heptane insoluble asphaltene content and associated spectrophotometry measurement as stored in the database. Alternatively, the correlation can be realized by regression analysis or other suitable processing. It is also contemplated that mole fraction can be used to quantify the n-heptane insoluble asphaltene content as part of the correlation between n-heptane insoluble asphaltene content and spectrophotometry measurement results associated therewith.

Also note that $n-C_6$ and $n-C_5$ can be used for asphaltene precipitation. In such case, the operations derive a correlation between weight fraction of $n-C_6$ insoluble (and/or $n-C_5$ insoluble) asphaltene content and spectrophotometry measurement results associated therewith.

Details of examples that follow the methodology of FIG. 2 for deriving and storing such a correlation between n-heptane insoluble asphaltene content and spectrophotometry measurement results are provided below as an Appendix.

Figure 3A:
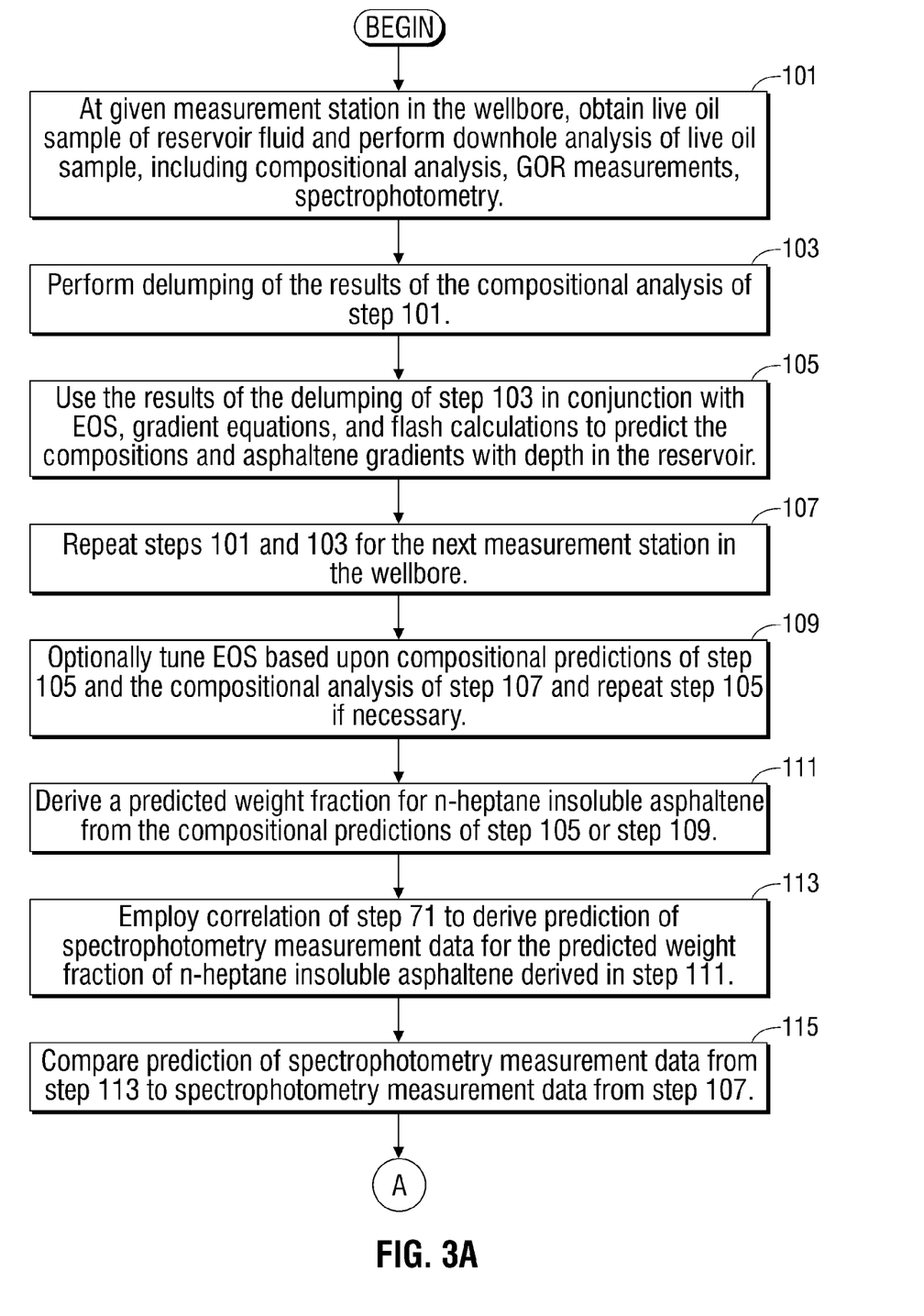
FIGS. 3A and 3B, collectively, are a flow chart of data analysis operations that includes downhole fluid analysis that predicts asphaltene content with depth. Such predictions and the correlations generated by the operations of FIG. 2 are used to predict spectrophotometry measurement data with depth. A comparison of predicted spectrophotometry measurement data and spectrophotometry measurement data measured by downhole fluid analysis at the corresponding depth is used to accurately detect compartmentalization and/or non-equilibrium hydrocarbon distribution in the reservoir of interest.
Figure 3B:
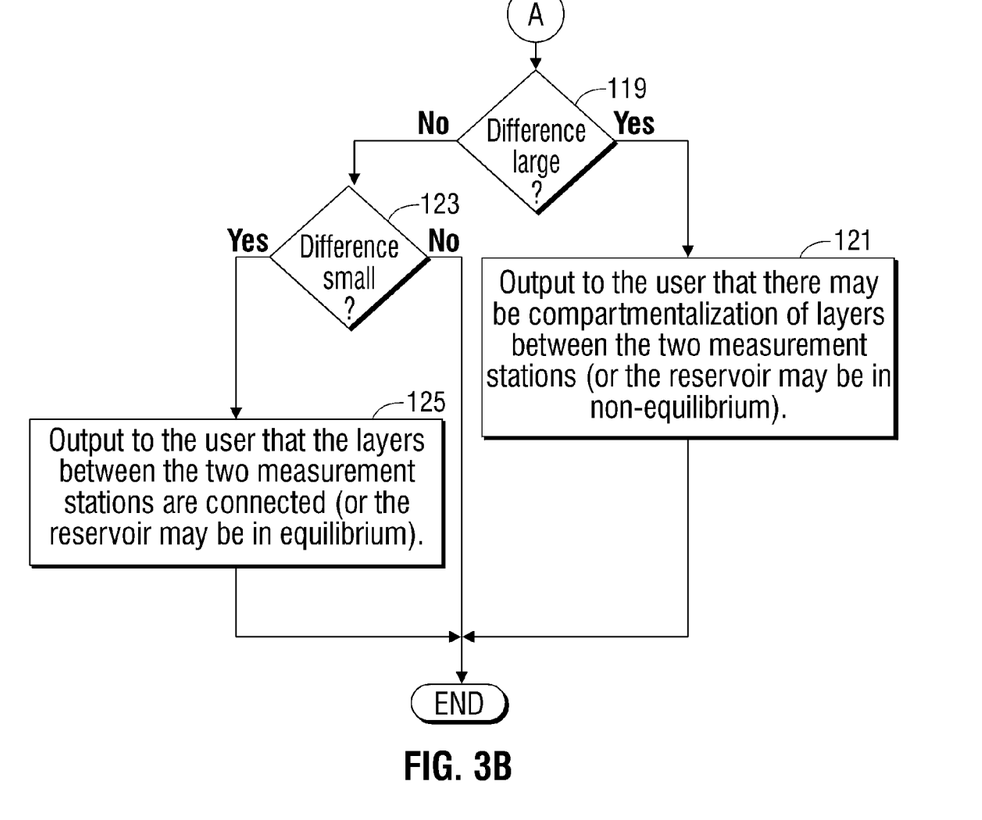

Turning now to FIGS. 3A and 3B, an exemplary methodology for determining reservoir compartmentalization or non-equilibrium in accordance with the present invention is shown.

The operations begin in step 101 by employing the DFA tool of FIG. 1 to obtain a sample of the formation fluid at the reservoir pressure and temperature (a live oil sample) at a measurement station in the wellbore (for example, a reference station). The sample is processed by the fluid analysis module 25. In the preferred embodiment, the fluid analysis module 25 performs spectrophotometry measurements that measure absorption spectra of the sample and translates such spectrophotometry measurements into concentrations of several alkane components and groups in the fluids of interest. In an illustrative embodiment, the fluid analysis module 25 provides measurements of the concentrations (e.g., weight percentages) of carbon dioxide ($CO_2$), methane ($CH_4$), ethane ($C_2H_6$), the C3-C5 alkane group including propane, butane, pentane, and the lump of hexane and heavier alkane components (C6+). The tool 10 also preferably provides a means to measure temperature of the fluid sample (and thus reservoir temperature at the station), pressure of the fluid sample (and thus reservoir pressure at the station), live fluid density of the fluid sample, gas-oil ratio (GOR) of the fluid sample. API gravity of the fluid sample, and formation volume factor (FVF) of the fluid sample.

In step 103, a delumping process is carried out to characterize the compositional components of the sample analyzed in step 101. Details of the exemplary delumping operations carried out as part of step 103 are described in detail in U.S. patent application Ser. No. 12/209,050, filed on Sep. 11, 2008, which is incorporated herein by reference.

In step 105, the results of the delumping process of step 103 are used in conjunction with equations of state (EOS) and flash calculations to predict compositional and asphaltene gradients with depth that take into account the impacts of, for example, gravitational forces, chemical forces, and thermal diffusion. The flash calculations provide for prediction of asphaltene content olive oil at downhole conditions at depth.

The EOS of step 105 include a set of equations that represent the phase behavior of the compositional components of the reservoir fluid. Such equations can lake many forms. For example, they can be any one of many cubic EOS, as is well known. Such cubic EOS include van der Waals EOS (1873), Redlich-Kwong EOS (1949). Soave-Redlich-Kwong EOS (1972). Peng-Robinson EOS (1976), Stryjek-Vera-Peng-Robinson EOS (1986) and Patel-Teja EOS (1982). Volume shift parameters can be employed as part of the cubic EOS in order to improve liquid density predictions, as is well known. Mixing rules (such as van der Waals mixing rule) can also be employed as part of the cubic EOS. A statistical association fluid theory "SAFT"-type EOS can also be used, as is well known in the art.

The EOS of step 105 are extended to predict compositional and asphaltene gradients with depth that take into account the impacts of, for example, gravitational forces, chemical forces, and thermal diffusion. To calculate compositional gradients with depth in a hydrocarbon reservoir, it is usually assumed that all components have zero mass flux, i.e., a stationary state in the absence of convection. To satisfy this assumption, a balance of driving forces or flux equations is applied. In the following example, three driving forces are taken into account: chemical potential, gravity, and thermal gradient. One vertical dimension model is applied as an example as well. The set of stationary state equations for a mixture with N-components are expressed as follows. The asphaltene gradient is provided by the asphaltene compositional component as part of the following equations.

$$\sum_{j=1}^{N} \left(\frac{\partial \mu_i}{\partial n_j}\right)_{T,P,n_{j\neq i}} \nabla n_j = (M_i - \bar{v}_i \rho)g - \frac{F_{Ti}}{T} \nabla T, \quad (1)$$

$$i = 1, 2, \ldots, N$$

where $\mu_i$, $v_i$, $M_i$, $g$, $\rho$ and $T$ are the chemical potential, the partial molar volume, and the molecular weight of component i, the gravitational acceleration, the density, and the temperature, respectively, $n_j$ is the mole number of component j. $F_{Ti}$ is the thermal diffusion flux of component i.

Since the chemical potential is a function of pressure, temperature and mole number, it can be expressed as:

$$\nabla \mu_i = \left(\frac{\partial \mu_i}{\partial P}\right)_{T,n} \nabla P + \left(\frac{\partial \mu_i}{\partial T}\right)_{P,n} \nabla T + \sum_{j=1}^{N} \left(\frac{\partial \mu_i}{\partial n_j}\right)_{T,P,n_{j\neq i}} \nabla n_j \quad (2)$$

The hydrostatic equilibrium is given by:

$$\nabla P = \rho g \quad (3)$$

According to thermodynamic relations, partial molar volume and entropy can be expressed as:

$$\bar{v}_i = \left(\frac{\partial \mu_i}{\partial P}\right)_{T,n} \quad (4)$$

and $$\bar{s}_i = -\left(\frac{\partial \mu_i}{\partial T}\right)_{P,n}$$

Therefore, the chemical potential change can be rewritten as:

$$\nabla \mu_i = \bar{v}_i \rho g - \bar{s}_i \nabla T + \sum_{j=1}^{N} \left(\frac{\partial \mu_i}{\partial n_j}\right)_{T,P,n_{j\neq i}} \nabla n_j \quad (5)$$

Substituting Eq. (5) into Eq. (2), we finally obtain:

$$\nabla \mu_i = M_i g - \left(\bar{s}_i + \frac{F_{Ti}}{T}\right) \nabla T \quad (6)$$

$$i = 1, 2, \ldots, N$$

The thermal diffusion flux of component i ($F_{Ti}$) can be calculated by different thermal diffusion models. An example is the Haase expression as described in Hasse. "Thermodynamics of Irreversible Processes." Addison-Wesley, Chapter 4, 1969, incorporated by reference herein in its entirety.

The EOS of 105 also employ Hash calculations that solve for fugacities of components that form at equilibrium. Details of suitable Hash calculations are described by Li in "Rapid Flash Calculations for Compositional Simulation." *SPE Reservoir Evaluation and Engineering*, October 2006.

In step 107, the DFA tool of FIG. 1 is used to obtain a sample of the formation fluid at the reservoir pressure and temperature (a live oil sample) at another measurement station in the wellbore and the downhole fluid analysis as described above with respect to step 101 is performed on this sample. In the preferred embodiment, the fluid analysis module 25 performs spectrophotometry measurements that measure absorption spectra of the sample and translates such spectrophotometry measurements into concentrations of several alkane components and groups in the fluids of interest. The tool 10 also preferably provides a means to measure temperature of the fluid sample (and thus reservoir temperature at the station), pressure of the fluid sample (and thus reservoir pressure at the station), live fluid density of the fluid sample, gas-oil ratio (GOR) of the fluid sample. API gravity of the fluid sample, and formation volume factor (FVF) of the fluid sample.

Optionally, in step 109 the EOS of step 105 are tuned based on a comparison of the compositional analysis of the DFA tool in step 107 and the predictions of composition gradient with depth derived by the EOS of step 105. In the event that the EOS is tuned, the compositional and asphaltene gradient predictions of step 105 can be recalculated from the tuned EOS. Tuning of the EOS of step 105 typically involves tuning volume translation parameters, binary interaction parameters, and/or critical properties of the components of the EOS. An example of EOS tuning is described in Reyadh A. Almehaideb et al., "EOS tuning to model full field crude oil properties using multiple well fluid PVT analysis." Journal of Petroleum Science and Engineering. Volume 26, Issues 1-4, pgs. 291-300, 2000, herein incorporated by reference in its entirety.

In step 111, a predicted weight fraction for n-heptane insoluble asphaltene is derived from the compositional predictions of step 105 or 109 by solving Eq. (6). Alternatively, a predicted weight fraction for n-$C_6$ or n-$C_5$ insoluble asphaltene can be derived from the compositional predictions of step 105 or 109.

In step 113, the correlation of step 71 of FIG. 2 is employed to predict spectrophotometry measurement data for the predicted weight fraction of n-heptane insoluble asphaltene derived in step 111.

In step 115, the predicted spectrophotometry measurement data derived in step 113 is compared to the spectrophotometry measurement data generated by the DFA tool in step 107.

In step 119, the operations check whether the difference result of the comparison of step 115 exceeds a predetermined threshold $T_e$. If so, the operations continue to step 121 to report to the operator that there may be compartmentalization of the layers between the two measurement stations. It is also possible to report to the user that the reservoir may be in non-equilibrium.

If in step 119 the difference result of the comparison of step 115 does not exceed a predetermined threshold $T_e$, the operations continue to step 123 to check whether difference result of the comparison of step 115 is less than a predetermined threshold $T_e$. If so, the operations continue to step 125 to report to the operator that the layers between the two measurement stations are connected. It is also possible to report to the user that the reservoir may be in equilibrium.

Note that the operations of steps 101-125 can be repeated for multiple station pairs within the borehole to provide for analysis of reservoir compartmentalization for multiple layers of the reservoir as required.

Figure 4:
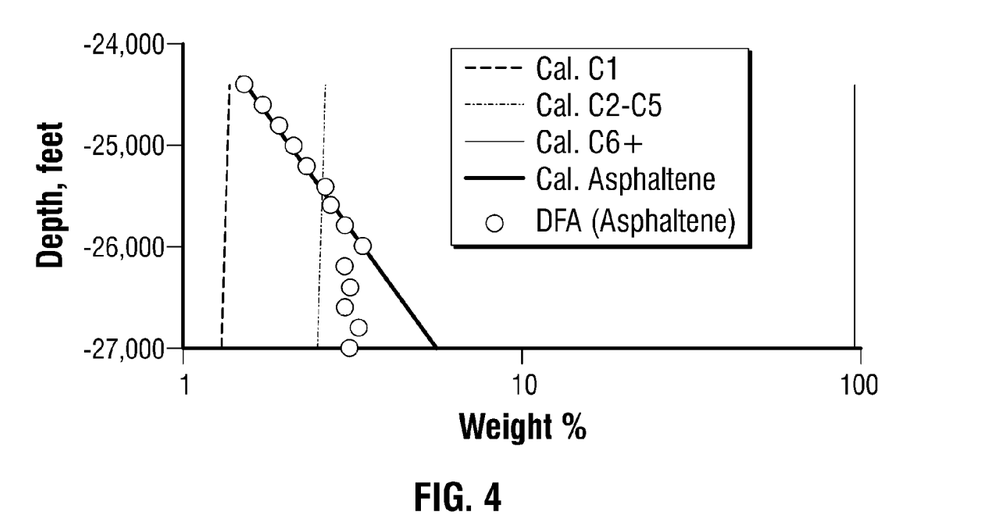
FIG. 4 is a plot of the compositional gradients calculated by solving the compositional gradient equations based on a reference point at −26,000 feet depth.

An example of the analysis provided by the present invention is illustrated in FIG. 4, which shows a plot of the compositional gradients calculated by solving the compositional gradient equations based on a reference point at −26,000 feet depth. It can be seen that the DFA data tracks the predicted asphaltene content above −26,000 feet, but below this depth the divergence of the DFA data from the predicted asphaltene content is apparent.

APPENDIX A

Sample: Ten dead oil samples of 100 ml each from different geographic regions were chosen for the experiments. The asphaltene contents ranged from 0.1 to 20 weight percent and the oil API gravity ranged from 10 to 40.

Equipment and Agents:
A Varian Gary 5000 spectrophotometer for color measurements
Rotary evaporator
Multiple evaporator
Hot plate
Mettler Toledo Balance, Model AG285
Heating mantle
Vacuum Filtration apparatus with a modified Millipore filter holder
Positive displacement pump
Round bottom flasks (250 ml), size 24/40
Condenser, size 24/40
Soxhlet extractor, top size 34/45, bottom size 24/40
Reducing adapter, size 34/45 to size 24/40
Transfer pipettes
Filter, 90 mm diameter, 0.45 micrometer laminated Fluoropore
Nitrogen
Sample vials, 22 ml
n-Heptane, HPLC grade (Residue on evaporation less than 5 ppm)
Dichloromethane (DCM), HPLC grade (Residue on evaporation less than 5 ppm).

Procedure A:
It is useful to measure the color of the n-heptane solution and know the exact dilution. To avoid n-heptane evaporation-caused uncertainty, one needs to measure the n-heptane solution before filtration. The mass is measured before and after filtration. A step by step procedure is described below. This procedure is employed for each one of the 10 different oil samples.

1. Weigh about 10 grams of sample, accurate to 0.0001 gram into a 500 ml glass flask with cap. Viscous samples (API gravity less than 20) and waxy samples should be heated to 60° C. for one hour and then shaken.
2. Add exactly 40:1 volume ratio of n-heptane.
3. Mix vigorously for 10 minutes with the cap on, and then allow the mixture to settle for 24 hours.
4. Filter the mixture to extract the precipitated asphaltene using 0.45 micron filter paper following these procedures:
   a. Form a filter paper into a cup shape using a modified Millipore filter holder. Weigh the filter paper.
   b. Set up the vacuum filtration apparatus.
   c. Pre-wet the filter paper with hot n-heptane before applying the vacuum. Filter the sample while hot, rinsing down the sides of the filter paper after each addition of sample with hot n-heptane.
   d. Rinse the flask three times to ensure maximum transfer of asphaltenes to the filter.
   e. Cover and set aside the flask. It will be used for the dichloromethane extraction as there may be asphaltenes stuck to the walls.
   f. Transfer the filtrate to a 500 ml glass bottle. Rinse the vacuum flask with hot n-heptane and then with DCM, transferring the rinses to the sample bottle. The filtrate can be discarded.
   g. Fold the filter, making sure that no asphaltenes are lost. If needed, a second weighed filter may be used to wrap the first one.
   h. Secure with a clean metal paper clip and wedge in a Soxhlet extractor so that the liquid covers the filter at the end of each cycle.
   i. Fill a new 250 ml flask with approximately 100 ml of fresh n-heptane.
   j. Wash the filters for two hours (minimum of 6 cycles) or until the solvent in the upper section of the Soxhlet extractor is clear, whichever occurs later. Ensure that the temperature of the n-heptane at the near full point in the cycle is at least 75° C. so that wax and oil are washed out of the asphaltene filter.
   k. When washing is complete, drain all heptane from the Soxhlet extractor into the flask, keeping the Alter with asphaltene inside the Soxhlet extractor.
   l. Add approximately 100 ml DCM to the first round bottom flask that was put aside after filtration,
   m. Place the flask under the Soxhlet extractor and extract until the solvent in the upper portion is clear.
5. Weight the extracted asphaltene.
6. Dissolve the extracted asphaltene into an appropriate amount of toluene (1 to 10 ml) and record weight percentage of asphaltene.
7. Perform color measurement with spectrophotometer on the asphaltene/toluene solution.
8. Store in a database the association between the weight percentage of asphaltene (recorded in 6) and the color measurement results of 7.
9. Optionally repeat the above procedure using n-$C_6$ for asphaltene precipitation.
10. Optionally repeat the above procedure using n-$C_5$ for asphaltene precipitation.

Procedure B:
1. From the ten dead oil samples, select three samples, one light, one medium, and one heavy oil sample.
2. For each sample perform the following:

3. Weigh about 10 grams of sample, accurate to 0.0001 gram into a topping flask.
4. Topping as per the following procedure: Set the temperature of the rotary evaporator water bath to 80° C. Flash the sample with nitrogen to eliminate oxygen contact. Weigh about 2 to 3 grams into a 250 ml round bottom flask using a 4 to 5 decimal place balance. Secure the flask on the evaporator. Slowly open the vacuum valve to full vacuum. Top the sample for a minimum of 90 minutes. Let the flask cool to room temperature and then weigh. Top the sample for another 15 minutes and then cool and weigh. Topping is considered to be finished when the sample weight change is less than 1% after 15 minutes of topping. Percent topping is calculated as (mass of topped oil)/(mass of un-topped oil)×100.
5. Dissolve the topped sample into 40-fold (volume) of n-heptane.
6. Mix per asphaltene precipitation procedure described above, then allow the mixture to settle.
7. Filter to extract precipitated asphaltene per item 4 of Procedure A as set forth above.
8. Weight the extracted asphaltene.
9. Dissolve the extracted asphaltene into an appropriate amount of toluene (1 to 10 ml) and record weight percentage of asphaltene.
10. Perform color measurement with spectrophotometer on the asphaltene/toluene solution.
11. Store in a database the association between the weight percentage of asphaltene (recorded in 9) and the color measurement results of 10.
12. Optionally repeat the above procedure using n-$C_6$ for asphaltene precipitation.
11. Optionally repeal the above procedure using n-$C_5$ for asphaltene precipitation.

After establishing The database of color measurements and weight percentage of asphaltene content, a correlation between coloration and asphaltene content weight percentage is generated.

There have been described and illustrated herein preferred embodiments of methods and apparatus for analysis of asphaltene gradients and applications thereof. While particular embodiments of the invention have been described, it is not intended that the invention be limited thereto, as it is intended that the invention be as broad in scope as the art will allow and that the specification be read likewise. Thus, while particular data processing methodologies and systems have been disclosed, it will be understood that other suitable data processing methodologies and systems can be similarly used. Also, while particular equations of state models and applications of such EOS have been disclosed for predicting properties of reservoir fluid, it will be appreciated that other equations of state and application thereof could be used as well. It will therefore be appreciated by those skilled in the art that yet other modifications could be made to the provided invention without deviating from its scope as claimed.

What is claimed is:

1. A method for characterizing a reservoir of interest comprising:
(a) obtaining a first reservoir fluid sample at a first downhole measurement station within a borehole that traverses the reservoir of interest:
(b) performing downhole fluid analysis of the first reservoir sample to characterize compositional components of the first reservoir sample:
(c) predicting compositional components with depth using the results of the downhole fluid analysis of (b);
(d) obtaining a second reservoir fluid sample at a second downhole measurement station within the borehole:
(e) performing spectrophotometry on the second reservoir fluid sample to derive spectrophotometry measurement data related to the second reservoir fluid sample:
(f) deriving predicted spectrophotometry measurement data for reservoir fluid at the second downhole measurement station based upon asphaltene concentration of the compositional components with depth predicted in (c) and correlation between asphaltene concentration and spectrophotometry measurement data:
(g) comparing the spectrophotometry measurement data of (e) and the predicted spectrophotometry measurement data of (f); and
(h) generating user output that characterizes the reservoir of interest based upon the comparing of (g).

2. A method according to claim 1, further comprising repealing steps (a)-(g) over a plurality of downhole measurement station pairs in order to generate user output that characterizes the reservoir of interest based upon the comparing of (g) for the plurality of downhole measurement station pairs.

3. A method according to claim 1, wherein the predicting of (e) involves a delumping process that characterizes the compositional components of the respective sample.

4. A method according to claim 1, wherein the predicting of (e) employs equations of state and Hash calculations to predict compositional and asphaltene gradients with depth.

5. A method according to claim 1, wherein the correlation relates insoluble asphaltene concentration to spectrophotometry measurement data.

6. A method according to claim 5, wherein the correlation is derived from a database of entries that associate insoluble asphaltene concentration to corresponding spectrophotometry measurement data.

7. A method according to claim 6, wherein the entries of the database are derived by extracting insoluble asphaltene from a number of different dead oil samples, dissolving the extracted insoluble asphaltene for each one of the samples in toluene, and recording the concentrations of the insoluble asphaltene in the solutions resulting therefrom, performing spectrophotometry of said solutions, and associating the recorded concentrations of insoluble asphaltene to the results of the corresponding spectrophotometry measurements.

8. A method according to claim 5, wherein the insoluble asphaltene is selected from the group including n-heptane insoluble asphaltene, n-hexane insoluble asphaltene, and n-pentane insoluble asphaltene.

9. A method according to claim 1, wherein the output relates to at least one of compartmentalization and non-equilibrium of the reservoir.

10. A method according to claim 1, wherein the output relates to at least one of connection of layers and equilibrium of the reservoir.

11. A system for characterizing a reservoir of interest, comprising:
(a) downhole tool means for obtaining at least first and second reservoir fluid samples at first and second downhole measurement stations, respectively, within a borehole that traverses the reservoir of interest, the tool comprising means for performing downhole fluid analysis of the first and second reservoir samples to characterize compositional components of the first and second reservoir samples, wherein the tool performs spectrophotometry on the first and second reservoir fluid samples to derive spectrophotometry measurement data related to the first and second reservoir fluid samples:

(b) means for predicting compositional components with depth using the results of the downhole fluid analysis related to the first reservoir fluid sample:

(c) means for deriving predicted spectrophotometry measurement data for reservoir fluid at the second downhole measurement station based upon asphaltene concentration of the compositional components with depth predicted by means (b) and correlation between asphaltene concentration and spectrophotometry measurement data:

(d) means for comparing the spectrophotometry measurement data generated by the tool means (a) as part of analysis of the second reservoir fluid sample and the predicted spectrophotometry measurement data of means (c); and (e) means for generating user output that characterizes the reservoir of interest based upon the comparing of means (d).

12. A system according to claim 11, wherein the means (a)-(c) are operated over a plurality of downhole measurement station pairs in order to generate user output that characterizes the reservoir of interest based upon the comparing of means (d) for the plurality of downhole measurement station pairs.

13. A system according to claim 11, wherein the predicting means (b) involves a delumping process that characterizes the compositional components of the respective sample.

14. A system according to claim 11, wherein the predicting means (b) employs equations of state and Hash calculations to predict compositional and asphaltene gradients with depth.

15. A system according to claim 11, wherein the correlation relates insoluble asphaltene concentration to spectrophotometry measurement data.

16. A system according to claim 15, wherein the correlation is derived from a database of entries that associate insoluble asphaltene concentration to corresponding spectrophotometry measurement data.

17. A system according to claim 16, wherein the entries of the database are derived by extracting insoluble asphaltene from a number of different dead oil samples, dissolving the extracted insoluble asphaltene for each one of the samples in toluene, and recording the concentrations of the insoluble asphaltene in the solutions resulting therefrom, performing spectrophotometry of said solutions, and associating the recorded concentrations of insoluble asphaltene to the results of the corresponding spectrophotometry measurements.

18. A system according to claim 15, wherein the insoluble asphaltene is selected from the group including n-heptane insoluble asphaltene, n-hexane insoluble asphaltene, and n-pentane insoluble asphaltene.

19. A system according to claim 11, wherein the output relates to at least one of compartmentalization and non-equilibrium of the reservoir.

20. A system according to claim 11, wherein the output relates to at least one of connection of layers and equilibrium of the reservoir.

* * * * *